(12) United States Patent
Hirano et al.

(10) Patent No.: US 8,333,957 B2
(45) Date of Patent: Dec. 18, 2012

(54) LIQUID DEODORANT COMPOSITION AND DEODORIZING METHOD

(75) Inventors: Kyoko Hirano, Kanagawa (JP); Kazuki Sugiyama, Kanagawa (JP); Hiroyasu Kumamoto, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 442 days.

(21) Appl. No.: 12/282,763

(22) PCT Filed: Mar. 22, 2007

(86) PCT No.: PCT/JP2007/055894
§ 371 (c)(1),
(2), (4) Date: Sep. 12, 2008

(87) PCT Pub. No.: WO2007/108511
PCT Pub. Date: Sep. 27, 2007

(65) Prior Publication Data
US 2009/0092571 A1 Apr. 9, 2009

(30) Foreign Application Priority Data

Mar. 22, 2006 (JP) ................. 2006-079797

(51) Int. Cl.
| A61L 9/00 | (2006.01) |
| A61L 9/01 | (2006.01) |
| A01N 65/00 | (2009.01) |
| A01N 43/16 | (2006.01) |
| A01N 25/00 | (2006.01) |
| A61K 36/00 | (2006.01) |
| A61K 31/35 | (2006.01) |
| A61K 47/00 | (2006.01) |

(52) U.S. Cl. ........ 424/76.1; 424/725; 514/456; 514/784
(58) Field of Classification Search ............ None
See application file for complete search history.

(56) References Cited

U.S. PATENT DOCUMENTS
2006/0165622 A1 7/2006 Hiramoto et al.

FOREIGN PATENT DOCUMENTS
| JP | 9-290014 | 11/1997 |
| JP | 9-290026 | 11/1997 |
| JP | 11-319051 | 11/1999 |
| JP | 2002-113080 | 4/2002 |
| JP | 2002-336338 | 11/2002 |
| JP | 2003-102819 | 4/2003 |
| JP | 2004-167218 | 6/2004 |
| JP | 2006-34300 | 2/2006 |

OTHER PUBLICATIONS

Kenichi; JP 2002 336338 A; Nov. 26, 2002; machine translation dated Feb. 9, 2011.*
Takezo et al.; JP 2003 102819 A; Apr. 8, 2003; machine translation dated Feb. 9, 2011.*
Masahide; JP 11 319051 A; Nov. 24, 1999; machine translation dated Feb. 9, 2011.*
Tanaka et al.; JP 2003 102819 A; Apr. 8, 2003; English translation dated Aug. 2011.*
Tomaru; JP 11 319051 A; Nov. 24, 1999; English translation dated Jul. 2011.*

* cited by examiner

*Primary Examiner* — Gina C Justice
*Assistant Examiner* — Michael B Pallay
(74) *Attorney, Agent, or Firm* — Fitzpatrick, Cella, Harper & Scinto

(57) ABSTRACT

The present invention relates to a double component type deodorant which comprises a first deodorant component A containing a liquid mixture containing a polyphenol and an acid agent and a second deodorant component B containing an alkali agent and an aqueous solvent. These deodorant components A and B may be separately stored in different storage parts. According to the invention, mixed type malodors in which at least two or more kinds of a sulfur-containing compound, aldehydes, lower fatty acids, amines, and the like are mixed can be efficiently deodorized.

13 Claims, No Drawings

LIQUID DEODORANT COMPOSITION AND DEODORIZING METHOD

TECHNICAL FIELD

The present invention relates to a double component type deodorant which is excellent in stability and also has a high effect of deodorizing a malodor containing plurality of malodor components. More specifically, it relates to a double component type deodorant excellent in stability and capable of efficiently deodorizing mixed type malodors in which at least two or more kinds of a sulfur-containing compound, aldehydes, lower fatty acids, amines, and the like are mixed, and particularly it relates to a double component type deodorant comprising a deodorant component A containing a polyphenol and an organic acid as active ingredients and a deodorant component B containing an alkali and an aqueous solvent, and a deodorizing product. Moreover, it relates to a deodorizing method using the same. Furthermore, the invention relates to a double component type deodorant exhibiting a high effect on reduction of mixed type malodor such as a smell of toilet, a smell of raw garbage, smells of feces or urine, or an animal smell, in which a sulfur-containing compound, aldehydes, lower fatty acids, amines, and the like are mixed, and excellent in stability.

BACKGROUND ART

In recent years, with diversification of lives, improvement of life level, changes and improvement of attitudes, and the like, attention has been paid to various points around one's life. One of them is existence of malodors. For example, as the malodors, there may be exemplified a smell generated in kitchen, a smell generated in toilet, smells of seat and breath, as well as a smell generated by a pet, a smell from industrial wastes, a smell generated at the time when human hair is subjected to permanent treatment or dyeing treatment, a smell generated when food organisms such as fishes are stored in storing devices such as refrigerator, and the like. These malodors cannot be avoided during human life. Thus, there have been actively investigated ways of coping the malodors, e.g., a so-called masking technology which make the malodors insensitive, a so-called deodorizing technology which traps the malodorous component, and the like.

On the other hand, hitherto, malodorous components have been analyzed and a sulfur-containing compound, aldehydes, lower fatty acids, various amines, and the like have been reported as smelly components. The malodorous components vary depending on various malodors as above, and also with regard to the malodors, there are known from relatively simple ones such as malodors comprising smelly component(s) belonging to a sulfur-containing compound to malodors comprising a large number of smelly components where compounds belonging to the sulfur-containing compound, aldehydes, lower fatty acids, various amines, and the like are contained in various ratios. For example, it is known that a smell of raw garbage resulting from vegetables, eggs, meats derived from domestic livestock, fishes and shellfishes, and the like is mixed malodors of hydrogen sulfide, methyl mercaptan, trimethylamine, ammonia, lower fatty acids, and the like; a smell of toilet resulting from animal excretion is mixed malodors of ammonia, methyl mercaptan, hydrogen sulfide, indole, and the like; a smell of cigarette is mixed malodors of ammonia, acetic acid, acetaldehyde, pyridine, hydrogen sulfide, and the like; and a human body smell is mixed malodors of ammonia, acetic acid, isovaleric acid, nonenal, and the like. Namely, as a method of coping the above malodors, it is understood that a method of coping complex malodors comprising a large number of smelly components as mentioned above is preferred.

As the above deodorants, deodorants comprising a plant extract have been reported (Patent Document 1, Patent Document 2, and the like). The deodorants have a characteristic of people friendliness since they are naturally occurring ones but the deodorizing effect is not satisfactorily sufficient.

As a deodorant composition improving such a point, there has been reported a technology where a colored substance obtained by reacting a polyphenol with an alkali ingredient is used as a deodorant active component (Patent Document 3). The deodorant composition is excellent in a deodorizing effect but has an inconvenience that embodiments of using the deodorant composition are limited for the reason that the active component is a colored substance.

On the other hand, as a technology for deodorizing malodors containing a plurality of malodorous components, there has been reported a deodorant wherein a deodorizing liquid containing an alkali agent and a deodorizing agent containing an acid agent are separately stored so that an acidic smell and an alkaline smell are simultaneously deodorized (Patent Document 4). The deodorant deodorizes both of the acidic smell and the alkaline smell at the same time through individual vaporization of the deodorizing liquid containing an alkali agent and the deodorizing agent containing an acid agent, which are stored separately, and thus may be called as a kind of vaporizing deodorant, which is not a deodorant wherein individual deodorizing agents are applied to a malodor source. While the above deodorants show a certain level of effect, they cannot be said to exhibit a sufficient deodorizing effect and thus leave a room for improvement.

Patent Document 1: JP-A-9-290014
Patent Document 2: JP-A-9-290026
Patent Document 3: JP-A-2004-167218
Patent Document 4: JP-A-2003-102819

DISCLOSURE OF THE INVENTION

Thus, an object of the invention is to provide a deodorant which is excellent in stability and also is capable of efficiently deodorizing mixed type malodors in which at least two or more kinds of a sulfur-containing compound, aldehydes, lower fatty acids, amines, and the like are mixed. Moreover, the deodorant of the invention has the above properties, and, particularly, it is to provide a deodorant which exhibits a deodorizing effect when applied to a malodor source.

During the extensive studies for solving the above problems, the present inventors have obtained a finding that the mixed type malodors in which the sulfur-containing compound, aldehydes, lower fatty acids, amines, and the like are mixed can be surprisingly effectively deodorized when a double component type deodorant comprising a deodorant component A containing a polyphenol and an organic acid incorporated thereto and maintaining acidic conditions and a deodorant component B containing an alkali component is applied to the malodor source. Based on the finding, they have further been studied and reached a deodorant having an effect more excellent than that of conventional deodorants and thus have accomplished the invention.

Namely, the invention relates to the following (1) to (16).

(1) A double component type deodorant comprising:
a deodorant component A containing a liquid mixture containing a polyphenol and an acid agent; and
a deodorant component B containing an alkali agent and an aqueous solvent.

(2) A double component type deodorant comprising:

a first deodorant component A containing a liquid mixture containing a polyphenol and an acid agent; and a second deodorant component B containing an alkali agent and an aqueous solvent.

(3) The double component type deodorant according to (1) or (2), wherein the polyphenol content is $10^{-7}$ to 10% by weight based on the deodorant component A.

(4) The double component type deodorant according to (1) or (2), wherein the acid agent is at least one selected from the group consisting of glycolic acid, lactic acid, glyceric acid, tartaric acid, citric acid, ascorbic acid, malic acid, succinic acid, fumaric acid, adipic acid, acidic amino acid, potassium chloride-hydrochloric acid buffer, potassium hydrogen phthalate-sodium hydride buffer, and sodium citrate-sodium hydroxide buffer.

(5) The double component type deodorant according to (1) or (2), wherein pH of the deodorant component A is 2 to 6.

(6) A deodorizing method, which comprises applying the double component type deodorant according to any one of (1) to (5) to a malodor source.

(7) The deodorizing method according to (6), which comprises:

applying a first deodorant component A containing a liquid mixture containing a polyphenol and an acid agent to a malodor source; and subsequently applying a second deodorant component B containing an alkali agent and an aqueous solvent to the malodor source.

(8) Use of the double component type deodorant according to any one of (1) to (5) for deodorizing a malodor.

(9) A double component type deodorizing product comprising:

two deodorant component-storing containers wherein at least parts thereof are mutually integrally molded and combined, a deodorant component A containing a liquid mixture containing a polyphenol and an acid agent, which is stored in one of the deodorant component-storing containers, and a deodorant component B containing an alkali agent and an aqueous solvent, which is stored in the other of the deodorant component-storing containers.

(10) The double component type deodorizing product according to (9), which comprises a structure wherein the deodorant component A flowing out of an outlet of the storing container in which the deodorant component A is stored and the deodorant component B flowing out of an outlet of the storing container in which the deodorant component B is stored are mutually mixed around the outlets thereof.

(11) An acidic liquid deodorant containing $10^{-7}$ to 10% by weight of a polyphenol and an acid agent and having pH of 2 to 6.

(12) The acidic liquid deodorant according to (11), wherein the acid agent is at least one selected from the group consisting of glycolic acid, glycerin acid, tartaric acid, citric acid, ascorbic acid, malic acid, succinic acid, fumaric acid, adipic acid, acidic amino acid, potassium chloride-hydrochloric acid buffer, potassium hydrogen phthalate-sodium hydride buffer, and sodium citrate-sodium hydroxide buffer.

(13) The acidic liquid deodorant according to (11) or (12), wherein the polyphenol is a polyphenol having an o-diphenol structure.

(14) The acidic liquid deodorant according to (11) or (12), wherein a polyphenol-containing plant extract is used as the polyphenol.

(15) A deodorizing method, which comprises applying an acidic liquid deodorant containing $10^{-7}$ to 10% by weight of a polyphenol and an acid agent and having pH of 2 to 6 to a malodor source.

(16) Use of an acidic liquid deodorant containing $10^{-7}$ to 10% by weight of a polyphenol and an acid agent and having pH of 2 to 6 for deodorizing a malodor.

In the above (1), the coexistence of an aqueous solvent in the deodorant component A is advantageous but is not always necessary. Moreover, the above liquid mixture also includes a mixture having an extremely high viscosity.

In the above (2), the first deodorant component means a first deodorant component to be applied to a malodor source and the second deodorant component means a second deodorant component to be applied to the malodor source subsequently to the above deodorant component applied.

In the above (10), the structure where components are mutually mixed around the outlets thereof means a structure in which the deodorant component A and the deodorant component B are mutually mixed immediately after or just before the components flow out of respective outlets. The case where the deodorant component A and the deodorant component B are partially mixed also means that they are mutually mixed. Namely, the invention also relates to an invention of a deodorizing method which comprises separately storing the deodorant component A and the deodorant component B in different storage parts, taking the above deodorant component A and deodorant component B out of the storing parts at the time when exhibition of a deodorizing junction is desired, combining the components, and applying them to a malodor source. In this connection, in the above (9) and (10), it is preferred to control the kinds and used amounts of the components constituting the above component A and component B so that pH shows alkaline when the deodorant component A and deodorant component B are combined and mixed.

According to the invention, there can be provided a double component type deodorant which is excellent in stability and also is capable of efficiently deodorizing mixed type malodors in which at least two or more kinds of a sulfur-containing compound, aldehydes, lower fatty acids, amines, and the like are mixed. A deodorant supposedly containing both of an acid and an alkali takes place an acid-alkali neutralization reaction in the deodorant, so that a deodorizing effect is hardly exhibited at the time when exhibition of a deodorizing function is desired and further the neutralization leads to loss of the deodorizing effect. Moreover, a polyphenol is unstable in an alkaline solution and thus is not suitable for storage but, in order to efficiently exhibit the deodorizing effect, it is necessary to maintain it at an alkaline side. The invention has solved these difficult points.

In particular, when a double component type deodorant comprising a first deodorant component A containing a liquid mixture containing a polyphenol and an acid agent and a second deodorant component B containing an alkali agent and an aqueous solvent is prepared and the first deodorant component A is first applied to a malodor source and then the second deodorant component B is applied to the malodor source, the above mixed type malodors can be efficiently deodorized.

Moreover, the deodorant of the invention is also a double component type deodorant wherein a deodorant component A containing a storage-stability-improved liquid mixture containing a polyphenol and an acid agent and a deodorant component B containing an alkali agent and an aqueous solvent are separately stored in different storage parts and the above deodorant component A and deodorant component B are taken out of the storing parts and combined at the time when exhibition of a deodorizing function is desired, so that a double component type deodorant excellent in stability, particularly storage stability, and deodorizing function can be provided. Furthermore, the double component type deodorant can be said to be also excellent in operability.

The invention is also relates to a double component type deodorizing product wherein these deodorant component A and deodorant component B are stored separately in a storing container.

BEST MODE FOR CARRYING OUT THE INVENTION

The invention will be described specifically.

The polyphenol to be used in the double component type deodorant in the invention will be described. The polyphenol to be used in the invention is not particularly limited so far as it is a polyphenol capable of attaining the intended purpose.

Specifically, the polyphenol to be used in the invention means a compound in which two or more hydrogen atoms on one identical benzene ring are substituted with hydroxyl groups, and glycosides thereof are also included as the polyphenol. Among them, hydroquinone and a polyphenol having an o-diphenol structure are preferred. The o-diphenol structure means such a structure that hydroxyl groups are directly substituted on the benzene ring and the hydroxyl groups are adjacent to each other.

Specific examples of the polyphenol include apigenin, apigenin glycosides, acacetin, isorhamnetin, isorhamnetin glycosides, isoquercitrin, epicatechin, epicatechin gallate, epigallocatechin, epigallocatechin gallate, aesculetin, ethyl protocatechuate salt, ellagic acid, catechol, gamma-acid, catechin, gardenin, gallocatechin, caffeic acid, caffeic esters, chlorogenic acid, kaempferol, kaempferol glycosides, quercetin, quercetin glycosides, quercetagenin, genistin, genistin glycoside, gossypetin, gossypetin glycosides, gossypol, 4-dihydroxyanthraquinone, 1,4-dihydroxynaphthalene, cyanidin, cyanidin glycosides, sinensetin, diosmetln, diosmetin glycosides, 3,4'-diphenyldiol, sinapic acid, stearyl-β-(3,5-di-t-butyl-4-hydroxyphenyl)propionate, spinacene, tangeritin, taxifolin, tannic acid, daphnetin, tyrosine, delphinidin, delphinidin glycosides, theaflavine, theaflavine monogallate, theaflavine bisgallate, tricetinidin, dopa, dopamine, naringenin, naringin, nordihydroguairetic acid, noradrenaline, nyaroauinone, vanillin, oatchouletin, herbacetin, vanillyl alcohol, vanitrope, vanillin propylene glycol acetal, vanillic acid, bis(4-hydroxyphenyl)sulfonic acid, bisphenol A, pyrocatechol, vitexin, 4,4'-biphenyldiol, 4-t-butylcatechol, 2-t-butylhydroquinone, protocatechuic acid, phloroglucinol, phenolic resins, procyanidin, prodelphinidin, phloretin, phloretin glycosides, fisetin, folin, fervasetin, fraxetin, phloridzin, paeonidin, paeonidin glycosides, pelargonidin, pelagugonidin glycosides, petunidin, petunidin glycosides, hesperetin, hesperidin, gallic acid, gallic esters (lauryl gallate, propyl gallate, butyl gallate), manjiferin, malvidin, malvidin glycosides, myricetin, myricetin glycosides, 2,2'-methylenebis(4-methyl-6-t-butylphenol), 2,2'-methylenebis(4-ethyl-6-t-butylphenol), 2,2'-methylenebis(4-methyl-6-t-butylphenol), 2,2'-methylenebis(4-ethyl-6-t-butylphenol), methyl atrarate, 4-methylcatechol, 5-methylcatechol, 4-methoxycatechol, 5-methoxycatechol, methylcatechol-4-carboxylic acid, 2-methylresorcinol, 5-methylresorcinol, morin, lignin, limocitrin, limocitrin glycosides, limocitrol, luteolin, luteolin glycosides, luteolinidin, luteolinidin glycosides, rutin, resorcin, resveratrol, resorcinol, leukocyanidin, leukodelphinidin, and the like.

Among these polyphenols, particularly preferred are flavonoids such as quercetin, epicatechin, and epigallocatechin and glycosides thereof; polyphenols having an o-diphenol structure such as gallic acid, gallic esters, chlorogenic acid, caffeic acid, caffeic esters, tannic acid, pyrocatechol, nordihydroguairetic acid, L-dopa, 4-methylcatechol, 5-methylcatechol, 4-methoxycatechol, and 5-methoxycatechol; and hydroquinone.

These polyphenols may be used each alone or as a mixture of two or more kinds of them.

Moreover, the above polyphenols can be prepared by known methods but commercially available products may be purchased. Moreover, they may be prepared by synthesis. Furthermore, polyphenol fractions prepared from plants can be employed.

in the invention, instead of the polyphenol, a polyphenol-containing plant extract can also be used. As the plant extract, one prepared by a known method may be used or a commercially available product may be used.

Examples of the above plant extract include plant extracts obtained through an extraction treatment by any usual methods from aloe, anise seeds, elder, eleutherococcus, psyllium, orange flower, allspice, oregano, valerian, chamomile, capsicum pepper, cardamon, cassia, garlic, caraway seeds, clove, cumin seeds, kola, coriander seeds, *Rhus lavanica*, saffron, zanthoxylum, juniper berry, cinnamon, ginger, star anise, St. Johns wart, celery seed, savory, sesame, pieplant, tarragon, turmeric, thistle, dill seed, nutmeg, nettle, hibiscus, hamamelis, birch, basil, bitter orange, fennel, primrose, fenugreek, verbena, bay laurel, hop, boldo, horseradish, poppy seed, gallnut, marigold, marrow, marjoram, mustard, Millefeuille, mint leaves, melissa, mace, lindane, gentian, rosehip, rosemary, *Rosmarinus officinalis*, sunflower seeds, grape pericarp, apple, carrot leaves, banana, strawberry, apricot, peach, plum, pineapple, Nashi pear, persimmon, cherry, papaya, mango, avocado, melon, loquat, fig, kiwi, prune, blueberry, black berry, raspberry, cranberry, coffee beans, cacao beans, grape seeds, grape fruits seeds, pecan nut, cashew nut, chestnut, coconut, peanut, walnut, green tea leaves, black tea leaves, oolong tea leaves, tobacco, perilla leaves, garden thyme, sage, lavender, spearmint, peppermint, spotted thistle, hyssop, sweet basil, marigold, dandelion, artichoke, *Matricaria chamomille, Agrimonia pilosa* var. *japonica*, licorice, anise, yarrow, eucalyptus, wormwood, balm, *Angelica pubescens*, fenugreek, *Capsicum annuum* var. *angulosum*, fennel, red pepper, coriander seeds, caraway seeds, fennel seeds, ginger, horseradish, *Origanum majorana, Origanum valgare*, mustard, parsley, pepper, savory, tarragon, queen lily, wasabi, dill seeds, citrus fruits, and the like. The plant extract may be used singly or a plurality of the plant extracts may be used in combination.

In this connection, the polyphenol compound and the polyphenol-containing plant extract may be used in combination.

The following will describe the acid agent to be used in the deodorant component A of the invention. The acid agent to be used in the invention is not particularly limited so far as it is an acid agent capable of attaining the intended purpose.

Specific examples of the acid agent include at least one selected from the group consisting of glycolic acid, glyceric acid, tartaric acid, citric acid, ascorbic acid, malic acid, succinic acid, fumaric acid, adipic acid, acidic amino acids, potassium chloride-hydrochloride buffer, potassium hydrogen phthalate-sodium hydride buffer, and sodium citrate-sodium hydroxide buffer. As the above acidic amino acids, aspartic acid, glutamic acid, and the like may be exemplified.

The deodorant component A of the invention contains the above polyphenol and acid agent as essential ingredients. Moreover, in addition to the above polyphenol and acid agent, a solvent such as an aqueous solvent can be further incorporated to form a liquid mixture. As desirable solvents, ethanol, isopropanol, propylene glycol, diethylene glycol, dipropylene glycol, and glycerin may be mentioned. Also, in the invention, purified water, ion-exchange water, pure water, or the like may be the aqueous solvent.

The above liquid mixture also includes a mixture having an extremely high viscosity. For example, it also includes a mixture which is stored in a resin-made tubular container and from which the content is taken out by pressing the container as needed.

In the deodorant component of the invention, in order to efficiently deodorize a sulfur-containing compound, the content of the polyphenol is $10^{-7}$ to 10% by weight, preferably $10^{-6}$ to 10% by weight, further desirably $10^{-6}$ to 5% by weight based on the total amount of the deodorant component A although the content depends on the polyphenol used. Moreover, the content of the acid agent is desirably 0.001 to 20% by weight, preferably 0.01 to 10% by weight based on the total amount of the deodorant component A although the content depends on the acid agent used. When the content of the polyphenol or the acid agent is less than the above range, a deodorizing effect is not sufficient and when the content of the polyphenol or the acid agent is more than the above range, the case is not preferred in view of handling properties and the like.

In this connection, an acidity of the deodorant component A depends on the polyphenol and acid agent used but is desirably pH of 1.0 to 6.0, preferably pH of 2.0 to 6.0. Within the range, the smell resulting from the sulfur-containing compound and amines can be efficiently deodorized and the polyphenol can stably exist.

The following will describe the alkali agent contained in the deodorant component B of the invention.

The above alkali agent is not particularly limited so far as it is an alkali agent capable of attaining the intended purpose. Various alkali agents can be used without particular limitation so far as they can mainly deodorize acidic smells resulting from hydrogen sulfide, isovaleric acid, formaldehyde, and the like, such as a smell of toilet, a smell of raw garbage, smells of faces or urine, and an animal smell.

Specific examples of the alkali agent include at least one selected from sodium carbonate, potassium carbonate, disodium hydrogen phosphate, dipotassium hydrogen phosphate, sodium citrate, potassium citrate, sodium hydroxide, potassium hydroxide, sodium carbonate-sodium hydrogen carbonate buffer, and disodium hydrogen phosphate-sodium hydroxide buffer.

The deodorant component B of the invention is a liquid deodorant composition containing the alkali agent and an aqueous solvent. As the aqueous solvent, water, pure water, ethanol, propylene glycol, glycerin, and the like may be mentioned.

In the deodorant component B of the invention, the content of the alkali agent is desirably 0.001 to 20% by weight, preferably 0.01 to 10% by weight based on the total amount of the deodorant component B although the content depends on the alkali agent used. When the content of the alkali agent is less than the above range, a deodorizing effect is not sufficient, and when the content of the alkali agent is more than the above range, the case is not preferred in view of handling properties and the like.

In this connection, a basicity of the deodorant component B depends on the alkali agent used but is desirably pH of 7.5 to 13.0, preferably pH of 8.0 to 12.5, more preferably pH of 8.5 to 12.0. Within the range, acidic smells can be efficiently deodorized.

In the invention, a fragrance suitable for individual deodorant components may be blended beforehand into the above deodorant component A and deodorant component B from the viewpoints of further improvement of deodorization performance, stability, odorous diffusivity, and the like.

In the invention, the fragrance to be blended into the deodorant component is not particularly limited so far as it is an organic compound generally vaporized into air at room temperature and is effective as a fragrance. The fragrance to be blended into the above component A is necessarily a fragrance stable to the polyphenol and the acid agent and, as the fragrance to be blended into the above component B, it is necessary to select a fragrance stable to the alkali agent.

When a fragrance unstable to the alkali agent is blended into the deodorant component B, with the lapse of time, there may easily occur a disfigurement of appearance of the deodorant component B through a decomposition of the fragrance, change in color, and precipitation, and destruction of harmony of aroma. Moreover, when a fragrance unstable to the acid agent and the polyphenol is blended into the deodorant component A, the same as above may occur, so that it is necessary to select a fragrance stable to individual components as individual fragrances to be blended into the deodorant component A and component B.

Into the deodorant component A of the invention, it is preferred to blend at least one selected from an alcohol-type aromachemical, an ester-type aromachemical, a hydrocarbon-type aromachemical, a lactone-type aromachemical, an ether-type aromachemical, and a natural origin aromatic material which are fragrances stable to the polyphenol and the acid agent. The amount of the fragrances to be blended is not particularly limited but, for example, desirably is 30 to 100% by weight, more preferably 30 to 80% by weight based on all the fragrances to be blended into the component A.

Into the deodorant component B, it is preferred to blend at least one selected from an alcohol-type aromachemical, an aldehyde-type aromachemical, a ketone-type aromachemical, an ether-type aromachemical, and a natural origin aromatic material which are fragrances stable to the alkali agent. The amount of the fragrances to be blended is not particularly limited but, for example, desirably is 30 to 100% by weight, more preferably 30 to 80% by weight based on all the fragrances to be blended into the component B.

In addition, to contain these fragrances in the above deodorant component B or component A leads to maintain a stable balanced aroma, respectively. The fragrance in the deodorant is useful in masking a malodor by the aroma of the fragrance, and in that case, it is desirable to be masked by a good-feeling and comfortable aroma to the user. In the invention, the fragrance to be used in the component A is a so-called fragrance compound, and it is desirable that the fragrance has a well-balanced aroma and a good-feeling and comfortable aroma to the user, and is a fragrance for masking. The component B is same as above, and it is desirable that the fragrance used in the component A has a well-balanced, a good-feeling and comfortable aroma to the user, and is a fragrance for masking.

Specific examples of the fragrances to be used in the invention are as follows.

As the alcohol-type aromachemical, there may be mentioned citronellol, geraniol, linarol, borneol, menthol, nerol, cis-3-hexenol, terpineol, tetrahydrolinarol, β-phenylethyl alcohol, cinnamic alcohol, anise alcohol, dimethylbenzyl carbinol, phenoxyethyl alcohol, sabinene hydrate, bacdanol, and santalol.

As the natural origin aromatic material, there may be mentioned peppermint oil, mentha oil, rosemary oil, eucalyptus oil, tea tree oil, orange oil, lavender oil, and geranium oil; and as the ether-type aromachemical, there may be mentioned galaxolide, roseoxide, linaroloxide, cineol, cedramber, dibenzyl ether, ambroxan, diphenyl oxide, β-naphthol methyl ether, and β-naphthol ethyl ether.

Moreover, with regard to the fragrance stable to the alkali agent, as the aldehyde-type aromachemical, there may be mentioned cis-3-hexenal, octanal, nonanal, decanal, citroneral, perillaldehyde, α-hexyl cinnamic aldehyde, helional, lilial, vanillin, and triplal; and as the ketone-type aromachemical, camphor, menthone, ionone, methylionone, tonalid, muscone, cyclopentadecane, cashmeran, damascone, damascenone, and cis-jasmone.

As the ester-type aromachemical, there may be mentioned citronellyl acetate, geranyl acetate, neryl acetate, benzyl acetate, terpinyl acetate, ethyl acetate, propyl acetate, butyl acetate, amyl acetate, bornyl acetate, menthyl acetate, p-tert-butylcyclohexyl acetate, o-tert-butylcyclohexyl acetate, phenylethyl acetate, and styrallyl acetate; as the hydrocarbon-type aromachemical, limonene, pinene, diphenylmethane, myrcene, and sabinene; and as the lactone-type aromachemical, coumarin, γ-undecalactone, cyclopentadecanolide, and γ-nonalactone.

In the invention, the amount of the fragrances to be blended into the deodorant component A or component B varies depending on the kinds and amounts of the chemical substances blended in the above component A or component B and thus is not categorically defined but, in order to enhance preferable aroma, the amount of respective fragrances stable to the deodorant component A or component B is preferably 0.01% by weight or more and is preferably 60% by weight or less based on the total amount of the deodorant component A or component B. When the amount is less than 0.1% by weight, stability of aroma with time and harmony of aroma are not sufficient, and when the amount is 60% by weight or more, preferable aroma cannot be enhanced.

In the invention, the other fragrances and solvents for fragrances can be further incorporated in a range where the advantages of the invention are not impaired. The other fragrances usable are mentioned in various documents, for example, "Perfume and Flavor Chemicals", Vol. I and II, Steffen Arctander, Allured Pub. Co. (1994) and "Gousei Kouryou, Kagaku to Syouhin Chishiki" written by Motoichi Indoh, The Chemical Daily Co., Ltd. (1996) and "Kaori no Hyakka" edited by Japan Perfumery & Flavoring Association, Asakura Publishing Co., Ltd. (1989) and "Perfumery Material Performance V. 3.3", Boelens Aroma Chemical Information Service (1996) and "Flower oils and Floral Compounds In Perfumery", Danute LaiaujisAnonis, Allured Pub. Co. (1993), and the like.

The following will mention representative examples of the other fragrances usable but the fragrances are not limited thereto so far as they fall within the range where the advantages of the invention are not impaired.

As the esters, for example, there may be used acrylate esters (methyl, ethyl, etc.), acetoacetate esters (methyl, ethyl, etc.), anisate esters (methyl, ethyl, etc.), benzoate esters (allyl, isoamyl, ethyl, geranyl, linalyl, phenylethyl, hexyl, cis-3-hexenyl, benzyl, methyl, etc.), anthranilate esters (cinnamyl, cis-3-hexenyl, methyl, ethyl, linalyl, isobutyl, etc.), N-methylanthranilate esters (methyl, ethyl, etc.), isovalerate ester (amyl, allyl, isoamyl, isobutyl, isopropyl, ethyl, octyl, geranyl, cyclohexyl, citronellyl, terpenyl, linalyl, cinnamyl, phenylethyl, butyl, propyl, hexyl, benzyl, methyl, rhodinyl, etc.), isobutyrate esters (isoamyl, geranyl, citronellyl, terpenyl, cinnamyl, octyl, neryl, phenylethyl, phenylpropyl, phenoxyethyl, butyl, propyl, Isopropyl, hexyl, benzyl, methyl, ethyl, linalyl, rhodinyl, etc.), undecylenate esters (allyl, isoamyl, butyl, ethyl, methyl, etc.), octanoate esters (allyl, isoamyl, ethyl, octyl, hexyl, butyl, methyl, linalyl, etc.), octenoate esters (methyl, ethyl, etc.), octynecarboxylate esters (methyl, ethyl, etc.), caproate esters (allyl, amyl, isoamyl, methyl, ethyl, isobutyl, propyl, hexyl, cis-3-hexenyl, trans-2-hexenyl, linalyl, geranyl, cyclohexyl, etc.), hexenoate esters (methyl, ethyl, etc.), valerate esters (amyl, isopropyl, isobutyl, ethyl, cis-3-hexenyl, trans-2-hexenyl, cinnamyl, phenylethyl, methyl, etc.), formate esters (anisyl, isoamyl, isopropyl, ethyl, octyl, geranyl, citronellyl, cinnamyl, cyclohexyl, terpinyl, phenylethyl, butyl, propyl, hexyl, cis-3-hexenyl, benzyl, linalyl, rhodinyl, etc.), crotonate esters (isobutyl, ethyl, cyclohexyl, etc.), cinnamate esters (allyl, ethyl, methyl, isopropyl, propyl, 3-phenylpropyl, benzyl, cyclohexyl, methyl, etc., succinate esters (monomenthyl, diethyl, dimethyl, etc.), acetate esters (anisyl, amyl, α-amylcinnamyl, isoamyl, isobutyl, isopropyl, isobornyl, isoeugenyl, eugenyl, 2-ethylbutyl, ethyl, 3-octyl, p-cresyl, o-cresyl, geranyl, α- or β-santalyl, cyclohexyl, cycloneryl, dihydrocuminyl, dimethylbenzylcarbinyl, cinnamyl, styrallyl, decyl, dodecyl, terpinyl, guanyl, neryl, nonyl, phenylethyl, phenylpropyl, butyl, furfuryl, propyl, hexyl, cis-3-hexenyl, trans-2-hexenyl, cis-3-nonenyl, cis-6-nonenyl, cis-3,cis-6-nonadienyl, 3-methyl-2-butenyl, heptyl, benzyl, bornyl, myrcenyl, dihydromyrcenyl, myrtenyl, methyl, 2-methylbutyl, menthyl, linalyl, rhodinyl, etc.), salicylate esters (allyl, isoamyl, phenyl, phenylethyl, benzyl, ethyl, methyl, etc.), cyclohexylalkanoate esters (ethyl cyclohexylacetate, allyl cyclohexylpropionate, allyl cyclohexylbutyrate, allyl cyclohexylhexanoate, allyl cyclohexyldecanoate, allyl cyclohexylvalerate, etc.), stearate esters (ethyl, propyl, butyl, etc.), sebacate esters (diethyl, dimethyl, etc.), decanoate esters (isoamyl, ethyl, butyl, methyl, etc.), dodecanoate esters (isoamyl, ethyl, butyl, etc.), lactate esters (isoamyl, ethyl, butyl, etc.), nonanoate esters (ethyl, phenylethyl, methyl, etc.), nonenoate esters (allyl, ethyl, methyl, etc.), hydroxyhexanoate esters (ethyl, methyl, etc.), phenylacetate esters (isoamyl, isobutyl, ethyl, geranyl, citronellyl, cis-3-hexenyl, methyl, etc.), phenoxyacetate esters (allyl, ethyl, methyl, etc.), furancarboxylate esters (ethyl lurancaroxylate, methyl furancarboxylate, hexyl furancarboxylate, isobutyl furanpropionate, etc.), propionate esters (anisyl, allyl, ethyl, amyl, isoamyl, propyl, butyl, isobutyl, isopropyl, benzyl, geranyl, cyclohexyl, citronellyl, cinnamyl, tetrahydrofurfuryl, tricyclodecenyl, heptyl, bornyl, methyl, menthyl, linalyl, terpinyl, α-methylpropionyl, β-methylpropionyl, etc.), heptanoate esters (allyl, ethyl, octyl, propyl, methyl, etc.), heptynecarboxylate esters (allyl, ethyl, propyl, methyl, etc.), myristate esters (isopropyl, ethyl, methyl, etc.), phenylglycidate esters (ethyl phenylglycidate, ethyl 3-methylphenylglycidate, ethyl p-methyl-β-phenylglycidate, etc.), 2-methylbutyrate esters (methyl, ethyl, octyl, phenylethyl, butyl, hexyl, benzyl, etc.), 3-methylbutyrate esters (methyl, ethyl, etc.), butyrate esters (anisyl, amyl, allyl, isoamyl, methyl, ethyl, propyl, octyl, guanyl, linalyl, geranyl, cyclohexyl, citronellyl, cinnamyl, neryl, terpenyl, phenylpropyl, β-phenylethyl, butyl, hexyl, cis-3-hexenyl, trans-2-hexenyl, benzyl, rhodinyl, etc.), hydroxybutyrate esters (methyl, ethyl, or menthyl 3-hydroxybuyrate, etc.), and the like.

As the alcohols, for example, there may be used aliphatic alcohols (isoamyl alcohol, 2-ethylhexanol, t-octanol, 3-octanol, 1-octen-3-ol, 1-decanol, 1-dodecanol, 2,6-nonadienol, nonanol, 2-nonanol, cis-6-nonenol, trans-2,cis-6-nonadienol, cis-3,cis-6-nonadienol, butanol, hexanol, cis-3-hexenol, trans-2-hexenol, 1-undecanol, heptanol, 2-heptanol, 3-methyl-1-pentanal, etc.), terpene alcohols (borneol, isoborneol, carveol, ceraniol, α- or β-santalol, citronellol, 4-thujanol, terpineol, 4-terpineol, nerol, myrcenol, myrtenol, dihydromyrcenol, tetrahydromyrcenol, nerolidol, hydroxycitronerol, farnesol, *perilla* alcohol, rhodinol, linalool, etc.), aromatic alcohols (anise alcohol, α-amylcinnamic alcohol, isopropylbenzylcarbinol, carvacrol, cuminic alcohol, dimethylbenzylcarbinol, cinnamic alcohol, phenylallyl alcohol, phenylethylcarbinol, β-phenylethyl alcohol, 3-phenylpropyl alcohol, benzyl alcohol, etc.), and the like.

As the aldehydes, for example, there may be used aliphatic aldehydes (acetaldehyde, octanal, nonanal, decanal, undecanal, 2,6-dimethyl-5-heptanal, 3,5,5-trimethylhexanal, cis-3, cis-6-nonadienal, trans-2,cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.), aromatic aldehydes (anisaldehyde, α-amylcinnamic aldehyde, α-methylcinnamic aldehyde, cyclamen aldehyde, p-isopropylphenylacetaldehyde, ethylvanillin, cuminaldehyde, salicylaldehyde, cinnamic aldehyde, o-, m- or p-tolylaldehyde, vanillin, piperonal, phenylacetaldehyde, heliotropin, benzaldehyde, 4-methyl-2-phenyl-2-pentenal, p-methoxycinnamic aldehyde, p-methoxybenzaldehyde, etc.), terpene aldehydes (geranial, citral, citronellal, α-sinensal, β-sinensal, perillaldehyde, hydroxycitronellal, tetrahydrocitral, myrtenal, cyclocitral, isocyclocitral, citronellyloxyacetaldehyde, neral, α-methylenecitronellal, myrac aldehyde, vernaldehyde, safranal, etc.), and the like.

As the ketones, for example, there may be used cyclic ketones (1-acetyl-3,3-dimethyl-1-cyclohexene, cis-jasmone, α-, β- or γ-irone, ethylmaltol, cyclotene, dihydronootkatone, 3,4-dimethyl-1,2-cyclopentadione, sotolone, α-, β-, γ- or δ-damascone, α-, β- or γ-damascenone, nootkatone, 2-sec-butylcyclohexanone, maltol, α-, β- or γ-ionone, α-, β- or γ-methylionone, α-, β- or γ-isomethylionone, furaneol, camphor, etc.), aromatic ketones (acetonaphthone, acetophenone, anisylideneacetone, raspberry ketone, p-methylacetophenone, anisylacetone, p-methoxyacetophenone, etc.), linear ketones (diacetyl, 2-nonanone, diacetyl, 2-heptanone, 2,3-heptanedione, 2-pentanone, methyl amyl ketone, methyl nonyl ketone, β-methyl naphthyl ketone, methylheptanone, 3-heptanone, 4-heptanone, 3-octanone, 2,3-hexanedione, 2-undecanone, dimethyloctenone, 6-methyl-5-heptyn-3-one, etc.), and the like.

As the acetals, for example, there may be used acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenylacetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, ambersage manufactured by Givaudan), ethyl acetoacetate ethylene glycol acetal, 2-pnenylpropanal dimethyl acetal, and the like.

As the phenols, for example, there may be used eugenol, isoeugenol, 2-methoxy-4-vinylphenol, thymol, carvacrol, guaiacol, chavicol, and the like.

As the ethers, for example, there may be used anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, α-terpinyl methyl ether, citronellyl ethyl ether, geranyl ethyl ether, rose-furan, theaspirane, decyl methyl ether, methyl phenylmethyl ether, and the like.

As the lactones, for example, there may be used γ-or δ-decalactone, γ-heptalactone, γ-nonalactone, γ- or δ-hexylactone, γ- or δ-octalactone, γ- or δ-undecalactone, δ-dodecalactone, δ-2-decenolactone, methyllactone, 5-hydroxy-8-undecenenoic acid δ-lactone, jasmine lactone, menthalactone, dihydrocoumarin, octahydrocoumarin, 6-methylcoumarin, and the like.

As the furans, for example, there may be used furan, 2-methylfuran, 3-methylfuran, 2-ethylfuran, 2,5-diethyltetrahydrofuran, 3-hydroxy-2-methyltetrahydrofuran, 2-(methoxymethyl)furan, 2,3-dihydrofuran, furfural, 5-methylfurfural, 3-(2-furyl)-2-methyl-2-propenal, 5-(hydroxymethyl)furfural, 2,5-dimethyl-4-hydroxy-3(2H)-furanone (furaneol), 4,5-dimethyl-3-hydroxy-2(5H)-furanone (sotolone), 2-ethyl-4-hydroxy-5-methyl-3(2H)-furanone (homofuranol), 5-ethyl-3-hydroxy-4-methyl-2(5H)furanone (homosotolone), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, and the like.

As the hydrocarbons, for example, there may be used α- or β-bisabolene, β-caryophyllene, p-cymene, terpinene, terpinolene, cadinene, farnesene, limonene, ocimene, myrcene, α- or β-pinene, 1,3,5-undecatriene, valencene, and the like.

Moreover, as the acids, for example, there may be used geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, and the like.

Furthermore, as the natural origin aromatic materials, for example, there may be used anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamom, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birth, capsicum, celery, tolu balsam, djenne, inmortel, benzoin, jasmine, cassia, tuberose, mignonette, marigold, mimosa, opopanax, orris, vanilla, licorice, and the like. The flavor components contained in these natural perfumes can be also used.

In the invention, an optional component used in a liquid deodorant can be incorporated into the deodorant component A or deodorant component B within a range where the advantages of the invention are not impaired. As the optional component usable, there may be mentioned a surfactant, a pigment, an antibacterial agent, an antiseptic, a fragranceretaining agent, a freeze-stabilizer, a deodorant base, an essential oil, a solvent, and the like.

Moreover, in the invention, an enzyme having a function capable of deodorizing or reducing a malodor may be coexisted. Moreover, a crude enzyme derived from a plant may be coexisted.

In the deodorizing method of the invention, it is advantageous to adopt a deodorizing method wherein one of the above deodorant components is applied to a malodor source and subsequently another component is applied to the malodor source. In particular, preferred one is a method which comprises first applying the deodorant component A containing a polyphenol and an acid agent to the malodor source, and subsequently applying the deodorant component B containing an alkali agent to the site to which the above component A has been applied. By the method, the above mixed type malodor can be extremely effectively deodorized.

In the invention, the ratio of the used amount of the above deodorant component A to the used amount of the deodorant component B at the time when they are applied to a malodor source is not particularly limited and the ratio widely varies depending on the kinds and amounts of the active ingredients contained in the deodorant components to be used, conditions of the malodor source to be deodorized, and the like. In this regard, the malodor source means, for example a site generating a malodor, such as raw garbage in kitchen, soil around watering facility, or toilet, or the neighborhood.

In the invention, the deodorant component A and deodorant component B may be applied to the malodor source at the same time.

In the invention, the above deodorant component A and deodorant component B can be separately stored to form a deodorizing product. The above separately storing means is not particularly limited, but a preferred means is to use a deodorant component-storing container which comprises containers in which the above deodorant component A and deodorant component B are separately stored and wherein at least part of these containers are mutually combined. The above two containers are preferably prepared by molding as an integrated container. Specifically, there may be exemplified a storing container wherein the deodorant component A and deodorant component B are stored in liquid states of the individual two liquids without mixing, in a container fitted with individual containers, e.g., a storing container having two storing parts storing the two liquids with a partition member in one container, in which the above individual components are stored, or a storing container wherein the above individual deodorizing liquids are stored in two independent containers and the independent containers are integrally combined with each other by a fixing mechanism or detachable mechanism such as fitting, jointing, or adhesion, or an integrated storing container wherein two independent type containers are set in a tray As a particularly preferred storing container, there may be mentioned a tubular container, which is fitted with a thin plate-type partition member or a tubular partition member having almost the same shape as that of the above container as the above partition member in the container. The above storing container is partitioned by the partition member to form two storing parts and they are separately stored in respective storing parts. When a deodorizing function is desired to be exhibited, the deodorant component A and deodorant component B are extruded from the outlets of respective storing parts, mutually mixed around the outlets (a site of the outlets in the extruding direction), and applied to a malodor source. As a specific example, a toothpaste tube can be exemplified but is not limited thereto in the invention.

Moreover, as a preferred container different from the above, there is a spray-type container. The container is classified into a gas-type one and a mist-type one and all these types of containers are included in the invention. In order to avoid complexity in explanation and difficulty in understanding, the explanation of the aforementioned types is omitted in the following.

A spray-type container fitted with two liquid-storing parts inside the container is also one of preferred storing containers of the invention, wherein the container is fitted with a hollow tube stored in respective liquid-storing parts and immersed in the deodorant components at one end, the above deodorant components are mutually combined in the vicinity of another end of the hollow tube, and the another end is connected to a spraying part. The deodorant component A and deodorant component B are stored in respective two storing parts of the above storing container. When a deodorizing function is desired to be exhibited, the deodorant component A and deodorant component B are passed through respective hollow tubes, mixed at a combined part of the hollow tubes, passed through an end part (outlet) of the hollow tube, and sprayed and applied through the spraying part to a malodor source.

Using the above deodorizing product, it becomes possible to deodorize mixed malodors. For example, there may be mentioned smells in kitchen such as a smell derived from raw garbage, a smell in refrigerator, and a smell generated at cooking foods, a smell in toilet, a smell generated at permanent wave treatment or hair-dying treatment, room smells such as a smell of pet's excretion, and the like. Moreover, acidic smells such as hydrogen sulfide, lower fatty acids, aldehydes and the like, alkaline smells such as ammonia and the like, and sulfur-containing compounds such as methyl mercaptan and the like can be efficiently deodorized at the same time.

Furthermore, when the fragrance composition is blended into individual deodorant components, the deodorant components are not decomposed, not changed in color, not precipitated, or not impaired in appearance and also the harmony of aroma is not destroyed with the lapse of time. Moreover, a stable aroma diffusivity can be maintained over a long period of time.

EXAMPLES

The following will specifically describe the invention by way of Examples and the like but the invention is by no means limited to the following examples.

Reference Example 1

Preparation of Tea Extract 1 kg of natural leaf tea (green tea) was extracted with 10 L of hot water at 90° C. with stirring for 1 hour and the tea leaves were removed by filtration to obtain 8.3 L of an extract solution. The solution was concentrated to 1 L and, after the addition of 1 L of acetone, the whole was stirred and then the resulting insoluble matter was removed by centrifugation. To the supernatant, 1 L of ethyl acetate was added and the whole was stirred and then allowed to stand for 30 minutes. The resulting ethyl acetate layer was concentrated under reduced pressure and converted into an aqueous layer, which was then freeze-dried to obtain 97 g of a tea extract containing tea phenol of 60% of purity.

Example 1

Preparation of Deodorant

A double component type deodorant was prepared by the following method.
(Preparation of Deodorant Component A)
After the tea extract of Reference Example 1 and citric acid were weighed in respective predetermined amounts, they were mixed and stirred to obtain a deodorant component A comprising 0.5% by weight of the tea extract, 0.5% by weight of citric acid, and 99% by weight of water. The pH was 2.7.
(Preparation of Deodorant Component B)
Sodium carbonate was weighed in a predetermined amount to obtain a deodorant component B comprising 0.5% by weight of sodium carbonate and 99.5% by weight of water. The pH was 11.2.

Application Example 1

Application of Double Component Type Deodorant to Permanent Wave Treated Hair

A permanent wave treated hair was immersed in the deodorant component A of Example 1 and then allowed to stand for 10 minutes. After the hair was drawn up and the above deodorant component A was removed by squeezing the hair, it was immersed in the deodorant component B of Example 1 and allowed to stand for 10 minutes. The hair was drawn up, squeezed, and washed with water, and then attached water was wiped off with a towel to obtain a permanent wave treated hair treated with the double component type deodorant.

Test Example 1

Deodorizing Effect of Double Component Type Deodorant of Example 1

A deodorizing effect of the double component type deodorant of Example 1 on the permanent wave treated hair was evaluated by the following sensory evaluation test.
(Operations)
After the permanent wave treated hair obtained in Application Example 1 was subjected to drying treatment at 37° C. for 1 hour, a sensory evaluation test was performed according to the following evaluation standard. In this connection, as a control, the permanent wave treated hair was washed with water in the same manner as in Application Example 1 and, after attached water was wiped off with a towel, it was dried in the same manner as above, then a deodorization-non-treated hair was used. The sensory evaluation was performed using the treated hair as a standard.
The results of the measurement are shown in Table 1. The numerical values in the table are average values of six panelists.

(Evaluation Standard)
5 permanent smell is intensely felt
4 permanent smell is
3 permanent smell is slightly felt
2 permanent smell is hardly felt
1 no permanent smell is felt Comparative Application Example 1

Application of Constitution Components of Double Component Type Deodorant to Permanent Wave Treated Hair After a permanent wave treated hair was immersed in a 0.5% by weight aqueous solution of the tea extract of Example 1, the hair was allowed to stand for 10 minutes. The hair was drawn up and the hair was squeezed and subsequently subjected to the same operations as in Application Example 1 to obtain a permanent wave treated hair.

Comparative Application Examples 2 to 3

Application of Constitution Components of Double Component Type Deodorant to Permanent Wave Treated Hair A permanent wave treated hair was obtained by performing the same operations as in Comparative Application Example 1 except that a 0.5% by weight aqueous solution of citric acid of Example 1 and the deodorant component B of Example 1 was used instead of the 0.5% by weight aqueous solution of the tea extract.

Comparative Application Example 4

Application of Constitution Components of Double Component Type Deodorant to Permanent Wave Treated Hair A permanent wave treated hair was obtained by performing the same operations as in Comparative Application Example 1 except that the deodorant component A of Example 1 was used instead of the 0.5% by weight aqueous solution of the tea extract.

Test Examples 2 to 5

Deodorizing Effect of Constitution Components of Double Component Type Deodorant of Example 1

A deodorizing effect of constitution components of double component type deodorant of Example 1 on the permanent wave treated hair was evaluated by the following sensory evaluation test.
(Operations)
The Permanent wave treated hair obtained in each of Comparative Application Examples 1 to 4 was subjected to sensory evaluation same as in Test Example 1.
The results of the measurement are shown in Table 1. The numerical values in the table are average values of six panelists.

TABLE 1

Results of Sensory Evaluation

| Non-treated (control example) | Application Example 1 | Comparative Application Example 1 | Comparative Application Example 2 | Comparative Application Example 3 | Comparative Application Example 4 |
|---|---|---|---|---|---|
| 5.0 | 1.8 | 3.0 | 3.6 | 4.2 | 2.7 |

Example 2

Preparation of Deodorant

A double component type deodorant was prepared by the following method.
(Preparation of First Deodorant Component)

After a pecannut extract (manufactured by NOF Corporation) and citric acid were weighed in respective predetermined amounts, they were mixed and stirred to obtain a first deodorant component comprising 0.5% by weight of the pecannut extract, 0.5% by weight of citric acid, and 99% by weight of water. The pH was 2.42.
(Preparation of Second Deodorant Component)

Sodium carbonate was weighed in a predetermined amount to obtain a second deodorant component comprising 0.5% by weight of sodium carbonate and 99.5% by weight of water. The pH was 11.2.

Example 3

Preparation of Deodorant

A double component type deodorant was prepared by the following method.
(Preparation of Deodorant Component A)

After gallic acid and citric acid were weighed in respective predetermined amounts, they were mixed and stirred to obtain a deodorant component A comprising 0.5% by weight of gallic acid, 0.5% by weight of citric acid, and 99% by weight of water. The pH was 2.42.
(Preparation of Deodorant Component B)

Sodium carbonate was weighed in a predetermined amount to obtain a second deodorant component comprising 0.5% by weight of sodium carbonate and 99.5% by weight of water. The pH was 11.2.

Example 4

Preparation of Deodorant

A double component type deodorant was prepared by the following method.
(Preparation of Deodorant Component A)

After the tea extract of Reference Example 1 and citric acid were weighed in respective predetermined amounts, they were mixed and stirred to obtain a deodorant component A comprising 0.5% by weight of the tea extract, 0.5% by weight of citric acid, and 99% by weight of water. The pH was 2.73.
(Preparation of Deodorant Component B)

Sodium carbonate was weighed in a predetermined amount to obtain a second deodorant component comprising 0.5% by weight of sodium carbonate and 99.5% by weight of water. The pH was 11.2.

Application Example 2

Application of Double Component Type Deodorant to Permanent Wave Treated Hair A permanent wave treated hair was immersed in the first deodorant component of Example 2 and then allowed to stand for 10 minutes. After the hair was drawn up and the above first deodorant component was removed by squeezing the hair, it was immersed in the second deodorant component of Example 2 and then allowed to stand for 10 minutes. Then the hair was drawn up and the hair was squeezed, and subsequently subjected to the same operations as in Application Example 1 to obtain a permanent wave treated hair treated with the double component type deodorant.

Application Example 3

Application of Double Component Type Deodorant to Permanent Wave Treated Hair A permanent wave treated hair was immersed in the second deodorant component of Example 2 and then allowed to stand for 10 minutes. After the hair was drawn up and the above first deodorant component was removed by squeezing the hair, it was immersed in the first deodorant component of Example 2 and then allowed to stand for 10 minutes. Then the hair was drawn up and the hair was squeezed, and subsequently subjected to the same operations as in Application Example 1 to obtain a permanent wave treated hair treated with the double component type deodorant.

Application Examples 4 to 5

Application of Double Component Type Deodorant to Permanent Wave Treated Hair A permanent wave treated hair treated with the double component type deodorant was obtained in the same operations as in Application Example 2 except that the deodorant of Examples 3 to 4 was used instead of the deodorant of Example 2.

Test Examples 6 to 9

Deodorizing Effect of Double Component Type Deodorant of Examples 2 to 4

A deodorizing effect of each of the double component type deodorants of Examples 2 to 4 on the permanent wave treated hair was evaluated by the following sensory evaluation test.
(Operations)

The permanent wave treated hair obtained in Application Examples 2 to 5 was subjected to sensory evaluation same as in Test Example 1.

The results of the evaluation are shown in Table 2.

TABLE 2

Results of Sensory Evaluation

| Non-treated (control example) | Application Example 2 | Application Example 3 | Application Example 4 | Application Example 5 |
|---|---|---|---|---|
| 5.0 | 2.0 | 3.2 | 2.2 | 2.8 |

Example 5

Preparation of Deodorant

A double component type deodorant was prepared by the following method.
(Preparation of Deodorant Component A)
After gallic acid and citric acid were weighed in respective predetermined amounts, they were mixed and stirred to obtain a deodorant component A comprising 0.25% by weight of gallic acid, 0.25% by weight of citric acid, and 99.5% by weight of water. The pH was 3.04.
(Preparation of Deodorant Component B)
Sodium carbonate was weighed in a predetermined amount to obtain a deodorant component B comprising 0.5% by weight of sodium carbonate and 99.5% by weight of water. The pH was 11.2.

Test Example 10

Deodorizing Effect of Double Component Type Deodorant of Example 5

A deodorizing effect of the double component type deodorant of Example 5 on the following mixed smells was evaluated by the following sensory evaluation test.
(Operations)
After a filter paper was placed on the bottom of a plastic cup having a bottom diameter of about 5 cm and a height of about 8 cm, 0.5 ml of model mixed smells having the following composition was dropped and infiltrated into the filter paper. Immediately, 1 mL of the deodorant component A of Example 5 was sprayed and the cup was quickly capped. After being allowed to stand for 5 minutes, the cup was uncapped and 1 mL of the deodorant component B was quickly sprayed, followed by immediate capping. After 5 minutes was passed, the cup was uncapped and the smell was subjected to sensory evaluation.
The sensory evaluation method was same as in Test Example 1. However, the evaluation standard was as follows. The results of the test are shown in Table 3.
(Model Mixed Odors)
The model mixed smells comprises 0.25% by weight of acetic acid, 0.25% by weight of acetaldehyde, 0.25% by weight of trimethylamine, and 0.125% by weight of methyl mercaptan, and 99.125% by weight of water.
(Evaluation Standard)
5 mixed smells are intensely felt
4 mixed smells are felt
3 mixed smells are slightly felt
2 mixed smells are hardly felt
1 no mixed smells are felt Test Example 11

Deodorizing Effect of Deodorant Component A of Example 5

A deodorizing effect of the deodorant component A of Example 5 on the mixed smells of Test Example 10 was evaluated by the following sensory evaluation test.
(Operations)
To the cup where the mixed smells same as in Test Example 10 had been infiltrated into the filter paper was sprayed 1 mL of the deodorant component A of Example 5, and immediately the cup was capped. After being allowed to stand for 5 minutes, the cup was uncapped and then subjected to the same operations as in Test Example 10, followed by sensory evaluation of the smell.
The results of the test are shown in Table 3.

Test Example 12

Deodorizing Effect of Deodorant Component B of Example 5

A deodorizing effect of the deodorant component B of Example 5 on the mixed smells of Test Example 10 was evaluated by performing the same operations as in Test Example 10 and subjecting the smell to sensory evaluation test.
The results of the test are shown in Table 3.

TABLE 3

Results of Sensory Evaluation

| Non-treated (control example) | Test Example 10 | Test Example 11 | Test Example 12 |
|---|---|---|---|
| 5.0 | 2.4 | 3.6 | 4.8 |

Example 6

Preparation of Deodorant

A double component type deodorant was prepared by the following method.
(Preparation of Deodorant Component A)
After gallic acid, malic acid, and 95% ethanol were weighed in respective predetermined amounts, they were mixed and stirred to obtain a deodorant component A comprising 1.0% by weight of gallic acid, 1.0% by weight of malic acid, 10.0% by weight of 95% ethanol, and 88% by weight of water. The pH was 2.3.
(Preparation of Deodorant Component B)
Sodium carbonate was weighed in a predetermined amount to obtain a deodorant component B comprising 1.0% by weight of sodium carbonate and 99.0% by weight of water. The pH was 11.4.

Test Example 13

Deodorizing Effect of Double Component Type Deodorant of Example 6

A deodorizing effect of the double component type deodorant of Example 6 on the following fish smell was evaluated by the following sensory evaluation test.

(Operations)

After a filter paper was placed on the bottom of a plastic cup having a bottom diameter of about 5 cm and a height of about 8 cm, 0.1 ml of a model fish smell having the following composition was dropped and infiltrated into the filter paper. Immediately, 0.2 mL of the deodorant component A of Example 6 was sprayed and the cup was quickly capped. After being allowed to stand for 2 minutes, the cup was uncapped and 0.2 mL of the deodorant component B was quickly sprayed, followed by immediate capping. After 2 minutes was passed, the cup was uncapped and the smell was subjected to sensory evaluation.

The sensory evaluation method was same as in Test Example 1. However, the evaluation standard was as follows. The results of the test are shown in Table 4.

(Model Fish Smell)

The model fish smell comprises 50% by weight of dipropylene glycol (DPG) containing 0.1% by weight of shrimp flavor and 50% by weight of DPG containing 0.1% by weight of sardine oil.

(Evaluation Standard)
5 fish smell is intensely felt
4 fish smell is felt
3 fish smell is slightly felt
2 fish smell is hardly felt
1 no fish smell is felt Example 7

Preparation of Deodorant

A double component type deodorant was prepared by the following method.
(Preparation of Deodorant Component A)

After the tea extract of Reference Example 1, citric acid, and 95% ethanol were weighed in respective predetermined amounts, they were mixed and stirred to obtain a deodorant component A comprising 1.0% by weight of the tea extract, 1.0% by weight of citric acid, 48.0% by weight of 95% ethanol, and 50% by weight of water. The pH was 3.5.
(Preparation of Deodorant Component B)

After sodium carbonate and 95% ethanol were weighed in respective predetermined amounts, they were mixed and stirred to obtain a deodorant component B comprising 1.0% by weight of sodium carbonate, 40.0% by weight of 95% ethanol, and 59.0% by weight of water. The pH was 12.2.

Test Example 14

Deodorizing Effect of Double Component Type Deodorant of Example 7

A deodorizing effect of the double component type deodorant of Example 7 on a pet excretion smell was evaluated by the following sensory evaluation test.
(Operations)

3 grams of cat litter after use was placed on the bottom of a plastic cup having a bottom diameter of about 5 cm and a height of about 8 cm. After a filter paper was placed on the cat litter, 0.2 mL of the deodorant component A of Example 7 was immediately sprayed and the cup was quickly capped. After being allowed to stand for 2 minutes, the cup was uncapped and 0.2 mL of the deodorant component B was quickly sprayed, followed by immediate capping. After 2 minutes was passed, the cup was uncapped and the smell was subjected to sensory evaluation.

The sensory evaluation method was same as in Test Example 1. However, the evaluation standard was as follows. The results of the test are shown in Table 4.
(Evaluation Standard)
5 pet excretion smell is intensely felt
4 pet excretion smell is felt
3 pet excretion smell is slightly felt
2 pet excretion smell is hardly felt
1 no pet excretion smell is felt Example 8

Preparation of Deodorant

A double component type deodorant was prepared by the following method.
(Preparation of Deodorant Component A)

After catechin (polyphenol GTP90, manufactured by Aiya Japan Corporation), citric acid, and a toothpaste (Tsubushio: manufactured by Kao Corporation) were weighed in respective predetermined amounts, they were mixed and stirred to obtain a deodorant component A comprising 0.5% by weight of catechin (polyphenol GTP90), 0.5% by weight of citric acid, and 99.0% by weight of the toothpaste. The pH was 5.8.
(Preparation of Deodorant Component B)

Sodium carbonate was weighed in a predetermined amount to obtain a deodorant component B comprising 0.5% by weight of sodium carbonate and 99.5% by weight of water. The pH was 8.75.

Test Example 15

Deodorizing Effect of Double Component Type Deodorant of Example 8

A deodorizing effect of the double component type deodorant of Example 8 on a smell of methyl mercaptan was evaluated by the following sensory evaluation test.
(Operations)

One drop of 5% by weight of an aqueous solution of methyl mercaptan Na was dropped into a mortar. To the mortar were added 0.5 g of the deodorant component A of Example 8, 1 g of the deodorant component B, and 2 mL of water. Then, the mortar was covered with a large bag so that the smell was not escaped and inside of the mortar was rubbed (brushed) with a toothbrush as tooth brushing. After one minute was passed, the cover was taken off and the smell was subjected to sensory evaluation. The sensory evaluation method was same as in Test Example 1. However, the evaluation standard was as follows.

The results of the test are shown in Table 4.
(Evaluation Standard)
5 smell of methyl mercaptan is intensely felt
4 smell of methyl mercaptan is felt
3 smell of methyl mercaptan is slightly felt
2 smell of methyl mercaptan is hardly felt
1 no smell of methyl mercaptan is felt

TABLE 4

Results of Sensory Evaluation

| Non-treated (control example) | Test Example 13 | Test Example 14 | Test Example 15 |
|---|---|---|---|
| 5.0 | 2.9 | 2.5 | 1.7 |

Example 9

Preparation of Deodorant

A double component type deodorant was prepared by the following method.
(Preparation of Deodorant Component A)

A polyphenol powder GTP90 was weighed and dissolved in water so that the concentration of catechin was 10,000 ppm, thereby an aqueous solution of catechin was prepared. Furthermore, citric acid was added in an amount of 0.1% to prepare a deodorant component A. The pH was 2.8.
(Preparation of Deodorant Component B)

Sodium carbonate was weighed in a predetermined amount to obtain a deodorant component B comprising 0.2% by weight of sodium carbonate and 99.8% by weight of water. The pH was 11.2.

Test Example 16

Deodorizing Effect of Double Component Type Deodorant of Example 9

A deodorizing effect of the double component type deodorant of Example 9 on the smell of methyl mercaptan was evaluated by the following sensory evaluation test.
(Operations)

Into a 300 mL Erlenmeyer flask were added 10 mL of the deodorizing test solution diluted with purified water and 10 µL of 1.5% aqueous solution of methyl mercaptan, and the flask was quickly capped with Parafilm, followed by shaking in a constant-temperature shaking water bath adjusted to 25° C. Thereafter, a small hole was made on the Parafilm on the Erlenmeyer flask and a gas detecting tube was quickly inserted therein to measure the concentration of the sulfur-containing compound which remained in the gas and was a malodor component. A deodorization rate was calculated according to the following expression. The shaking time was 10 minutes and purified water was used as a blank.

$$\text{Deodorization rate}(\%) = 100 \times \{1 - (A/B)\}$$

In the above expression, A means the measured concentration of the malodor components and B means the concentration of the malodor components measured in the control. As the control, 10 mL of purified water was used.

The results are shown in Table 5.

TABLE 5

| Content of catechin (ppm) | 0 | 1 | 10 | 100 | 1000 | 5000 |
|---|---|---|---|---|---|---|
| Deodorization rate (%) | 0 | 75 | 90 | 90 | 90 | 90 |
| Concentration of methyl mercaptan (ppm) | 80 | 20 | 8 | 8 | 8 | 8 |

While the invention has been described in detail with reference to specific examples thereof, it will be apparent to one skilled in the art that various changes and modifications can be made therein without departing from the spirit and scope of the invention.

The present application is based on Japanese Patent Application No. 2006-079797 filed on Mar. 22, 2006, and the contents are incorporated herein by reference.

Also, all the references cited herein are incorporated as a whole.
Industrial Applicability According to the present invention, a double component type deodorant which is excellent in stability and also is capable of efficiently deodorizing mixed type malodors in which at least two or more kinds of a sulfur-containing compound, aldehydes, lower fatty acids, amines, and the like are mixed can be provided.

In particular, when a double component type deodorant comprising a first deodorant component A containing a liquid mixture containing a polyphenol and an acid agent and a second deodorant component B containing an alkali agent and an aqueous solvent is prepared and the first deodorant component A is first applied to a malodor source and then the second deodorant component B is applied to the malodor source, the above mixed type malodors can be efficiently deodorized.

The invention claimed is:

1. A deodorizing method, which comprises the steps of:
    selecting a double component type deodorant comprising a liquid deodorant component A comprising an admixed polyphenol and an acid agent; and a liquid deodorant component B comprising an aqueous alkali agent and an aqueous solvent;
    applying said deodorant component A without component B to a malodor source; and
    subsequently applying said deodorant component B without component A to the malodor source.

2. The deodorizing method according to claim 1, wherein the polyphenol content is $10^{-7}$ to 10% by weight based on the deodorant component A.

3. The deodorizing method according to claim 2 or 1, wherein the acid agent is at least one member selected from the group consisting of glycolic acid, lactic acid, glyceric acid, tartaric acid, citric acid, ascorbic acid, malic acid, succinic acid, fumaric acid, adipic acid, acidic amino acid, potassium chloride-hydrochloric acid buffer, potassium hydrogen phthalate-sodium hydride buffer, and sodium citrate-sodium hydroxide buffer.

4. The deodorizing method according to claim 3, wherein the polyphenol is a polyphenol having an o-diphenol structure.

5. The deodorizing method according to claim 4, wherein said polyphenol is provided by a polyphenol-containing plant extract.

6. The deodorizing method according to claim 2 or 1, wherein the deodorant component A has a pH of 2 to 6.

7. The deodorizing method according to claim 6, wherein the acid agent is at least one member selected from the group consisting of glycolic acid, glyceric acid, tartaric acid, citric acid, ascorbic acid, malic acid, succinic acid, fumaric acid, adipic acid, acidic amino acid, potassium chloride-hydrochloric acid buffer, potassium hydrogen phthalate-sodium hydride buffer, and sodium citrate-sodium hydroxide buffer.

8. The deodorizing method according to claim 7, wherein the polyphenol is a polyphenol having an o-diphenol structure.

9. The deodorizing method according to claim 8, wherein said polyphenol is provided by a polyphenol-containing plant extract.

10. The deodorizing method according to claim 6, wherein the polyphenol is a polyphenol having an o-diphenol structure.

11. The deodorizing method according to claim 10, wherein said polyphenol is provided by a polyphenol-containing plant extract.

12. The deodorizing method according to claim 2 or 1, wherein the polyphenol is a polyphenol having an o-diphenol structure.

13. The deodorizing method according to claim 12, wherein said polyphenol is provided by a polyphenol-containing plant extract.

* * * * *